(12) United States Patent
Norddahl et al.

(10) Patent No.: US 10,781,143 B2
(45) Date of Patent: Sep. 22, 2020

(54) METHOD AND PLANT FOR TREATMENT OF ORGANIC WASTE

(71) Applicant: Renew Energy A/S, Svendborg (DK)

(72) Inventors: Birgir Norddahl, Ringe (DK); Anne Kjaerhuus Nielsen, Odnese S (DK)

(73) Assignee: RENEW ENERGY USA LLC, Svendborg (DK)

( * ) Notice: Subject to any disclaimer, the term of this patent is extended or adjusted under 35 U.S.C. 154(b) by 347 days.

(21) Appl. No.: 14/902,739

(22) PCT Filed: Jul. 8, 2014

(86) PCT No.: PCT/EP2014/064638
§ 371 (c)(1),
(2) Date: Jan. 4, 2016

(87) PCT Pub. No.: WO2015/004146
PCT Pub. Date: Jan. 15, 2015

(65) Prior Publication Data
US 2016/0176768 A1   Jun. 23, 2016

Related U.S. Application Data

(60) Provisional application No. 61/844,086, filed on Jul. 9, 2013.

(51) Int. Cl.
*C05D 1/00* (2006.01)
*C02F 9/00* (2006.01)
(Continued)

(52) U.S. Cl.
CPC .................. *C05D 1/00* (2013.01); *C02F 9/00* (2013.01); *C05B 17/00* (2013.01); *C05C 3/00* (2013.01);
(Continued)

(58) Field of Classification Search
CPC .... C02F 11/04; C02F 1/06; C02F 1/20; C02F 1/441; C02F 2101/16; C02F 9/00;
(Continued)

(56) References Cited

U.S. PATENT DOCUMENTS 6,368,849 B1   4/2002   Norddahl ................ 435/262
7,014,768 B2   3/2006   Li et al. .................. 210/603
(Continued)

FOREIGN PATENT DOCUMENTS

DE   10221505 A1   11/2003
DK   9500113 U3    5/1995
(Continued)

OTHER PUBLICATIONS

International Search Report and Written Opinion in PCT/EP14/064638, dated Oct. 24, 2014, PCT.
(Continued)

*Primary Examiner* — Gautam Prakash
*Assistant Examiner* — Lydia Edwards
(74) *Attorney, Agent, or Firm* — Licata & Tyrrell P.C.

(57) ABSTRACT

The present invention relates to methods and plants for the treatment of an organic waste material, wherein waste is subjected to anaerobic fermentation in a biogas digester; effluent is mechanically separated from the biogas digester into a concentrated fraction and a liquid fraction; the liquid fraction is heated to a high temperature below the boiling point of the liquid; the heated liquid is introduced to a flash column to partially remove volatile carbon dioxide, the pH of the liquid is elevated and ammonia is removed from the liquid.

8 Claims, 6 Drawing Sheets

(51) Int. Cl.
<table>
<tr><td>C05B 17/00</td><td>(2006.01)</td></tr>
<tr><td>C05F 3/00</td><td>(2006.01)</td></tr>
<tr><td>C05F 17/00</td><td>(2020.01)</td></tr>
<tr><td>C05F 17/02</td><td>(2006.01)</td></tr>
<tr><td>C12M 1/107</td><td>(2006.01)</td></tr>
<tr><td>C12M 1/00</td><td>(2006.01)</td></tr>
<tr><td>C12M 1/02</td><td>(2006.01)</td></tr>
<tr><td>C05F 17/10</td><td>(2020.01)</td></tr>
<tr><td>C05F 17/40</td><td>(2020.01)</td></tr>
<tr><td>C05F 17/50</td><td>(2020.01)</td></tr>
<tr><td>C05F 17/60</td><td>(2020.01)</td></tr>
<tr><td>C05F 17/964</td><td>(2020.01)</td></tr>
<tr><td>C05C 3/00</td><td>(2006.01)</td></tr>
<tr><td>C02F 1/44</td><td>(2006.01)</td></tr>
<tr><td>C02F 101/16</td><td>(2006.01)</td></tr>
<tr><td>C02F 1/20</td><td>(2006.01)</td></tr>
<tr><td>C02F 1/06</td><td>(2006.01)</td></tr>
<tr><td>C02F 11/04</td><td>(2006.01)</td></tr>
</table>

(52) U.S. Cl.
CPC ............... *C05F 3/00* (2013.01); *C05F 17/10* (2020.01); *C05F 17/15* (2020.01); *C05F 17/40* (2020.01); *C05F 17/50* (2020.01); *C05F 17/60* (2020.01); *C05F 17/964* (2020.01); *C12M 21/04* (2013.01); *C12M 29/20* (2013.01); *C12M 41/14* (2013.01); *C12M 47/18* (2013.01); *C02F 1/06* (2013.01); *C02F 1/20* (2013.01); *C02F 1/441* (2013.01); *C02F 11/04* (2013.01); *C02F 2101/16* (2013.01); *Y02E 50/343* (2013.01); *Y02P 20/145* (2015.11); *Y02W 30/43* (2015.05); *Y02W 30/47* (2015.05)

(58) Field of Classification Search
CPC .. C05B 17/00; C05C 3/00; C05D 1/00; C05F 17/0018; C05F 17/0027; C05F 17/0045; C05F 17/0054; C05F 17/0063; C05F 17/0258
See application file for complete search history.

(56) References Cited

U.S. PATENT DOCUMENTS

<table>
<tr><td>2008/0302722 A1*</td><td>12/2008</td><td>Burke</td><td>C02F 1/20<br>210/603</td></tr>
<tr><td>2009/0206028 A1</td><td>8/2009</td><td>Jiang et al.</td><td>210/603</td></tr>
<tr><td>2012/0315209 A1*</td><td>12/2012</td><td>Bisson</td><td>B01D 61/58<br>423/352</td></tr>
<tr><td>2013/0047852 A1*</td><td>2/2013</td><td>Kirchmayr</td><td>C02F 1/06<br>95/266</td></tr>
</table>

FOREIGN PATENT DOCUMENTS

<table>
<tr><td>WO</td><td>WO9942423</td><td>8/1999</td></tr>
<tr><td>WO</td><td>WO12109737</td><td>8/2012</td></tr>
<tr><td>WO</td><td>WO13091094</td><td>6/2013</td></tr>
</table>

OTHER PUBLICATIONS

International Search Report and Written Opinion in PCT/EP14/064638, dated Jan. 12, 2016, PCT.

* cited by examiner

METHOD AND PLANT FOR TREATMENT OF ORGANIC WASTE

This patent application is a U.S. National Stage Application of PCT/EP2014/064638 filed Jul. 8, 2014 and claims the benefit of priority from U.S. Provisional Application Ser. No. 61/844,086, filed Jul. 9, 2013, the teachings of each of which are herein incorporated by reference in their entirety.

FIELD OF THE INVENTION

The present invention relates to methods and plants for treatment of manure and other organic waste materials.

BACKGROUND OF THE INVENTION

To meet the increasing worldwide demands for food, intensive livestock production has become more widespread. This trend will undoubtedly continue in the future. While providing important benefits in terms of increased yield and a more efficient production process, intensive livestock production has negative environmental consequences due to the large amount of organic waste that is produced. Intensive production of pigs and dairy cattle results in a large amount of manure that can present serious environmental problems if not handled correctly. At the same time, biomass production, for the specific purpose of producing energy, has proliferated thereby encouraging pursuits to increase utilisation of all components arising from the biological process. Both the environmental and the utility topic have increased demands for technologies turning nutrients from waste and biomass in general into useful products thus minimizing environmental impact and maximizing profit.

Organic fertilizers such as manure contain plant nutrients that are essential for crop production. However, livestock manure contains phosphorus (P) and potassium (K) and nitrogen (N) in a ratio which often does not correspond to the needs of the crop. If nutrients are applied at a higher rate than the plant uptake, there is a great risk of nutrient leaching and runoff that will pollute surface water and groundwater. Splitting manure into three separate N, P and K fertilizer products will allow correct fertilization of the crops, thereby reducing the risk of leaching.

Danish utility model No. DK 95 00113 U3 describes a plant for the treatment of liquid manure, in which the liquid manure is converted to compost, fertilizers, water and biogas. The plant comprises: 1) a filtration unit for separating fibrous and particulate material having a size of over 1 mm and particles less than 1 mm from the liquid, the fibrous and particulate material having a size of over 1 mm being used, for example, as compost; 2) a digester for the production of biogas; 3) an ultrafiltration unit that retains bacteria and suspended organic material and returns such material to the biogas digester; 4) a desulphurisation unit that removes hydrogen sulphide from the biogas before the biogas is used for the production of heat and power; and 5) a reverse osmosis unit, in which the permeate stream from the ultra filter is separated into a water fraction and a fertilizer concentrate fraction.

A separation plant for liquid manure, referred to as BIOREK® of Bioscan A/S (Odense, Denmark) has been described. The BIOREK® plant is based on the plant described in DK 95 00113 U3 and U.S. Pat. No. 6,368,849 and further contains, between the ultrafiltration unit and the reverse osmosis unit, an ammonia stripper for the removal of ammonia and carbon dioxide from the permeate stream from the ultra filter. The BIOREK® plant is described at e.g. http://www with the extension gec.jp/jsim_data/waste/waste_6/html/doc_555.html of the World Wide Web and in EP 98902971.5.

The feed to the BIOREK® system is separated into a fibre fraction and a fibreless liquid, the fibres and particles above a certain size being removed from the feed so that fibrous material does not interfere with proper operation of the ultra filter of the system. The benefit from this operation is a fibre-free liquid that will not block the ultra filter membrane coupled to the digester. However, the gas potential in the fibre separated from the feed is not utilized.

This reverse osmosis (RO) operation normally requires that the feed to the RO be at neutral pH, which necessitates that the effluent from the ammonia stripping be neutralised. This generally is performed, e.g. in the BIOREK® plant, by adding acids. However, addition of acids increases the costs of operation.

U.S. Pat. No. 7,014,768 discloses a process for removal and recovery of nutrients from digested manure which results in a bio fertilizer with high nitrogen content.

Published U.S. Patent Application No. 2009/0206028 discloses a system for processing by-products of anaerobic digestion of waste materials involving phosphorus and nitrogen removal stages, while also scrubbing the biogas.

SUMMARY OF THE INVENTION

An aspect of the present invention relates to a method for the treatment of an organic waste material.

The method comprises using a grinder/macerator, an extruder, a thermal treatment unit, a shredder and/or screen to produce a homogeneous liquid waste material which is fed to the biogas digester for anaerobic fermentation; heating the liquid effluent stream to a high temperature below the boiling point of the liquid; introducing the heated liquid to a suitable flash column to partially remove volatile carbon dioxide while at the same time elevating the pH of the liquid due to escape of carbon dioxide; removing ammonia from the ammonia rich liquid phase via a means for stripping ammonia to create ammonium sulphate in a scrubber unit; neutralizing the ammonia free liquid with biogas, flash gas and/or acetic or citric acid; and treating the clear liquid phase remaining after ammonia removal in a reverse osmosis unit to obtain a potassium rich fraction useful as a fertilizer concentrate and a clean water fraction. In one embodiment, sodium hydroxide is also added to the heated liquid prior to ammonia stripping to further insure that the pH is in a range for optimal ammonia stripping.

Another aspect of the present invention relates to treatment plants for conducting a method of the present invention.

In addition to providing for cost effective waste treatment, the methods and plants of the present invention are useful in increasing biogas produced from liquid wastes, producing phosphate rich fertilizers and/or producing ammonium sulfate rich fertilizers and/or producing potassium rich fertilizers.

DETAILED DESCRIPTION OF THE INVENTION

Figure 1:
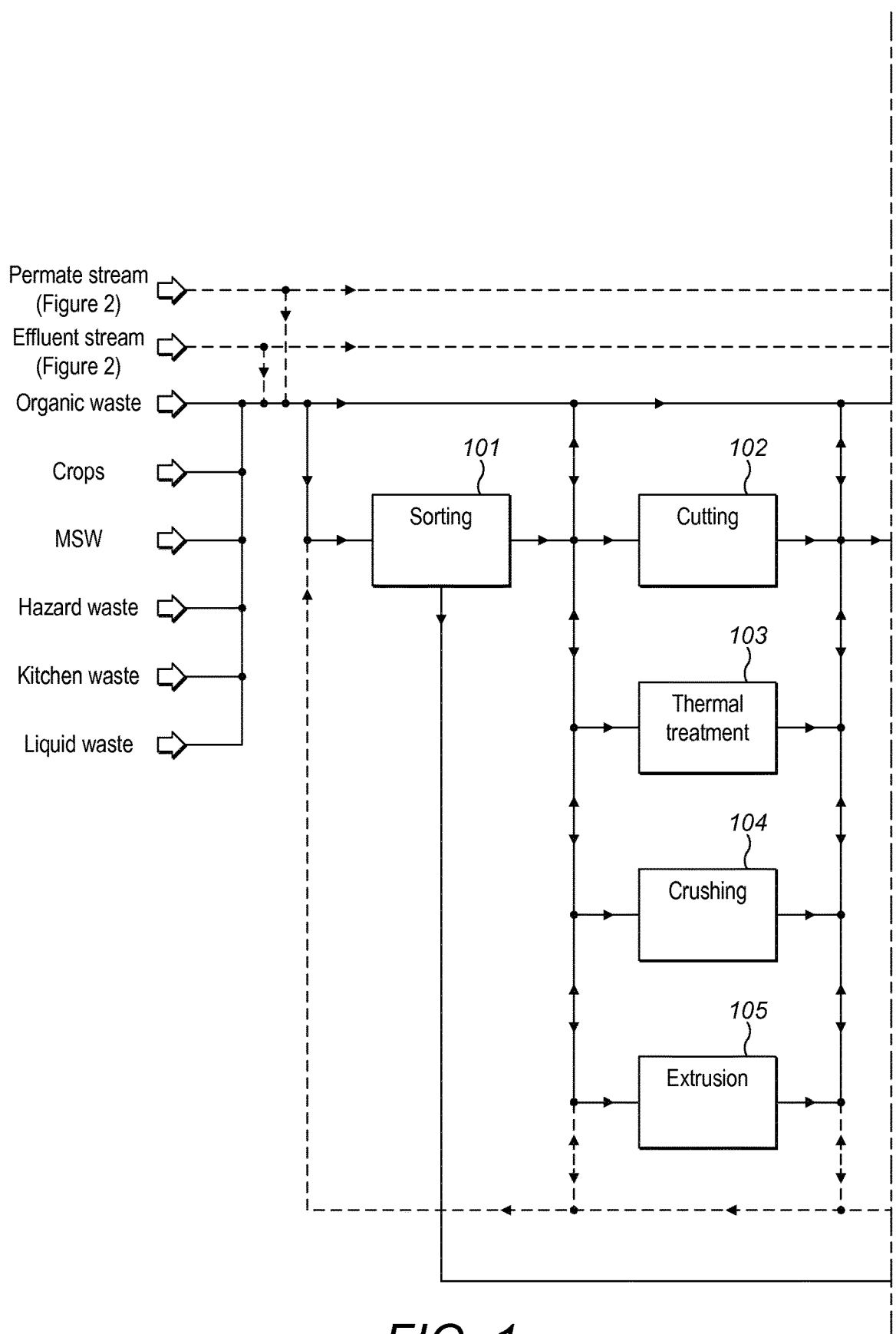
FIG. 1 is a diagram showing components of one embodiment of the biogas process of the present invention, including pre-treatment, anaerobic digestion, biogas cleaning and biogas utilization. Different alternative embodiments of the process are shown in this figure.
Figure 1:
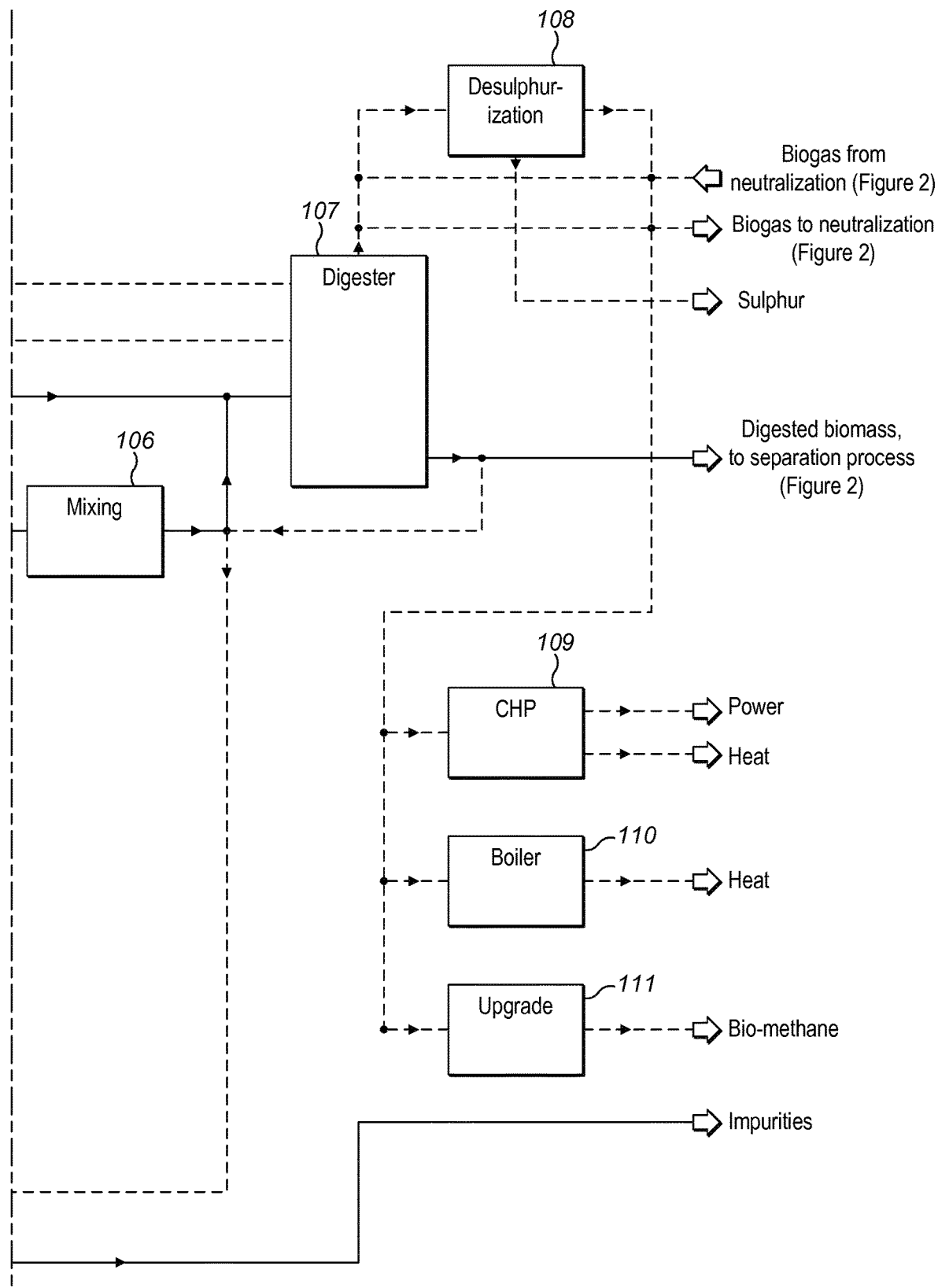

The present invention provides methods and plants for the treatment of manure and other organic waste materials, which can be digested in a microbial process. The methods and plants of the present invention are suitable for treatment of any organic waste material, including wastes from households, industries and agricultures, including sewage from institutions such as hospitals, effluents from biofuel production as well as manure from livestock production. The methods and plants are particularly suitable for treating the manure that results from intensive livestock production, e.g. intensive production of pigs and dairy cattle. It will be clear to persons skilled in the art upon reading this disclosure, that the methods and plants of the present invention are equally applicable to all types of organic waste materials.

The organic waste material to be treated in accordance with the present invention is, in one embodiment, fed directly to the digester. In other embodiments, the organic waste material is treated in a pre-treatment process prior to entering the digester. The present invention is in no way limited by the pre-treatment methods described herein.

The organic waste material to be treated in accordance with the present invention, e.g. manure, typically comprises not only liquid with a variety of organic and inorganic components dissolved therein, but also a certain amount of fibrous and/or particulate matter suspended therein. Accordingly, in one embodiment of the present invention, the organic waste material to be fed to a biogas digester is first ground in a grinder or macerator allowing all of the fibres to be fed to the biogas digester. In one embodiment fibrous and particulate material above a certain size is reduced in size by a macerator before the feed is subjected to anaerobic fermentation and subsequent steps in the process, as such larger particles will tend to prolong the digestion process, thereby reducing treatment efficiency and increasing costs. The organic material is therefore typically shredded to reduce larger fibres and particles, optionally after having been treated with a macerator. The shredded feed can subsequently be subjected to anaerobic fermentation in the biogas digester. This grinding or maceration step increases the amount of accessible organic material for the bacteria in the digester and allows for increased biogas production. Further, the grinding operation decreases the particles and fibres in the organic waste material to a size where the biological process of decomposition is improved. Organic material such as crops can also be treated in an extruding process to open the biomass and create a larger surface. This will also increase the amount of accessible organic material for the bacteria and allow for increased biogas production.

Food/household waste can be treated in a shredding and sorting process, prior to anaerobic digestion, as well. In one embodiment this shredding and sorting process involves crushing/ripping, magnet separation and food/household waste grinding for separation of impurities from the food/household waste.

In other embodiments, fresh organic material and organic material from other pre-treatment stages are treated in a thermal treatment process prior to entering the digester. For example, when the organic waste is characterized as a health risk due to content of pathogenic microorganisms, the organic material can be treated in a thermal process. A nonlimiting example of such a sterilization process comprises heating the biomass to a temperature of 133° C. and a gauge pressure of 3 bar for 20 minutes. Another nonlimiting example of a sanitation process which can be used comprises heating the organic material to a temperature of 70° C. for 60 minutes. In cases where the organic waste being fed to the digester contains components in a form which is known to be recalcitrant, i.e. having a low degradability, this waste may be first treated in a vacuum cooker. In one embodiment, the vacuum cooker comprises a pressure tank, which can be heated to temperatures between 120° C. and 165° C. (248° F.-329° F.). In advance of the heating procedure, the vacuum cooker is evacuated to a vacuum of between 0.1 bar (g)(1.45 psi) and 0.2 bar (g) (2.9 psi). The vacuum cooker treatment will kill pathogens. Food/household waste can also be treated in a vacuum cooker as this treatment softens the waste to a degree where solid, not-digestible components (batteries, glass, etc.) can be separated from the organic fraction by a screening operation.

Further, for the treatment of sewage from, for example, households, institutions or industry, a coarse screen having openings of, for example, about 2-3 cm for removing large non-organic objects from the sewage can be incorporated as part of the vacuum cooker. In one embodiment, the course screening is performed externally and subsequent to the vacuum cooker.

Organic material resulting from pre-treatments and/or untreated organic material is in one embodiment subsequently mixed in a mixing tank prior to feeding of the digester. The mixing tank provides a means for controlling the supply and/or transfer of liquid to be treated in the biogas digester, thereby maintaining a suitable load in the biogas digester. Further, the mixing tank provides an area where particles such as grains of sand, which are undesired in the subsequent treatment process, can sediment, while suspended organic particles can be led in a controlled manner, together with the liquid, to the biogas digester.

From the mixing tank, manure and/or other organic material is led to the biogas digester, in which anaerobic fermentation takes place. Various biogas digesters are known and the present invention is in no way limited by the reactor type used. In one embodiment, the biogas digester is a plug-flow digester, where the feed is introduced in one end of a tubular or channel like container and the liquid is pushed forward through several chambers with or without agitation. In another embodiment, the digester is conical in shape at the bottom with a waste inlet near the bottom and two different outlets. In this embodiment, the liquid to be treated is typically pumped into the biogas digester via an inlet in the lower part of the digester. The digester may be stirred to maintain good contact between digesting microorganisms and the feed components. In one embodiment, stirring is accomplished by a top-mounted agitator with a large rotor and with a driving motor placed outside the digester.

The temperature in the biogas digester can be varied as desired. In one embodiment, the temperature is maintained at a temperature suitable for mesophilic bacteria. In one embodiment, the temperature range is about 20-40° C. In one embodiment the temperature range is about 30-40° C. In one embodiment, the temperature range is about 35-37° C.

In another embodiment, the temperature is maintained at more than 50° C., the regime for thermophilic bacteria. It has been found that a higher temperature results in a faster reaction in the digestion process resulting in a smaller digester volume as well as a higher degree of reduction of pathogenic bacteria and viruses. For most purposes, including the treatment of liquid manure, the bacteria responsible for the anaerobic fermentation are those bacteria that are naturally present in the liquid waste being treated. However, in some embodiments, it may be advantageous to supplement the native bacteria by adding one or more desired bacteria cultures to the biogas digester or to the organic material.

The biogas digester is designed to have a suitable size for the intended type and amount of organic material to be treated. Suitable size of the biogas digester is important for optimal fermentation. Suitable size of the biogas digester is also important for sufficient degradation of the organic components in the digester to obtain a maximal digestion and gas production. When the waste material being treated is manure from livestock, the organic load in the biogas digester is preferably below about 10 kg volatile solids per cubic meter per day (kg VS/m$^3$/d, determined according to Danish Standard 207:1985, a standard method of volatile solid determination, as loss on ignition at 550° C. for 1 hour), e.g. not more than about 8 kg volatile solids per cubic meter per day, preferably not more than about 5 kg volatile solids per cubic meter per day. However, for other types of liquid wastes, the load in the digester may be greater. For example, it is believed that a load of up to about 20 kg VS/m$^3$/d will be suitable when treating distillery waste, because the content of sugar and alcohol in such waste enhances the fermentation process.

Although the residence time in the biogas digester will vary depending on such factors as the nature of the waste material, the organic matter content, the bacteria mix present and the temperature of the liquid, it has been found that for liquid mixed wastes, a residence time derived from the organic load of the digester measured as kg Volatile Solids (VS)/m$^3$/day at a level of about 1-6 kgVS/m$^3$/day, or about 2-5 kgVS/m$^3$/day, or about 4-5 kgVS/m$^3$/day, is generally suitable.

Biogas produced by the fermentation is removed from the biogas digester via an outlet at or near the top of the digester vessel. In one embodiment, when the biogas contains hydrogen sulphide, the gas is subjected to a desulphurisation process to remove the hydrogen sulphide. In one embodiment, the desulphurisation process is performed after mixing the biogas with air. The desulphurisation process may be performed using known methods and apparatus such as, but not limited to, ochre ore filters, iron filing filters, iron hydroxide filters, bark filters or a sulphite wash process. The resulting biogas contains predominately methane and some carbon dioxide, and only very small amounts of other gases.

When the biogas contains less than 100 ppm H$_2$S, the desulphurization step is not required.

The resulting biogas has many uses including, but in no way limited to, powering gas motors or generators, use at the plant for generating electricity and heat, and heating of nearby homes. Power from the biogas can also be sold to power companies for use in their grids.

In one embodiment the biogas is used as a source for further treatment in a biogas up-grading unit. The further treatment in the biogas up-grading unit involves removal of CO$_2$ and other gases from the biogas to create methane of a minimum 95% purity, preferably 99% purity. Methane from the upgrading plant is suitable for distribution to the natural gas grid. The biogas upgrading process can comprise, but is in no way limited to, water scrubbing and/or pressure swing adsorption.

In one embodiment, the effluent from the digester is led back to the pre-treatment step and/or mixing tank. In another embodiment, the digester effluent is led to an intermediate storage tank from which the effluent is fed to a mechanical separator. In yet another embodiment, the digester effluent is led directly to the mechanical separator.

In some embodiments, buffer tanks are placed as intermediate storage tanks between all or some unit operations of the plant, whereby feed to the unit operations are fed to the buffer tanks prior to entering the unit operation.

In one embodiment, the mechanical separator comprises a decanter centrifuge. The decanter centrifuge separates the effluent into two fractions, a concentrated fraction and a liquid fraction. The concentrated fraction comprises typically between 12-16% of the total flow to the decanter centrifuge with a total solids content of between 20% and 42% useful as a combination of fertilizer and soil conditioner. Typically 75% of phosphor led to the decanter centrifuge ends in the concentrated fraction. The liquid fraction comprises typically between 84% and 88% of the total flow to the decanter centrifuges with a total solids content corresponding to the mass balance for the total flow.

Alternative separators useful in the present invention include, but are not limited to, screw presses, chamber filter presses and ordinary sloped screens.

Following mechanical separation, the liquid fraction, also referred to herein as mechanical separation liquid effluent, is in one embodiment subjected to a further suspended solid removal process. In another embodiment, when the total suspended solid content is already reduced to a range suitable for CO$_2$ flash and ammonia stripping, the mechanical separation liquid effluent is fed directly to the flash or stripper. In a third embodiment, the mechanical separation liquid effluent is recycled to the digester, for example for dilution purposes.

In one embodiment the suspended solid removal is an ultra-filtration producing a concentrate stream comprising typically about 20-40% of the feed stream and a permeate stream, which is a sterile and particle free stream containing most of the soluble substances in the mechanical separation liquid effluent. Alternative suspended solid removal process units include, but are not limited to, micro filtration units (MF), nano filtration units (NF), reverse osmosis units (RO), and high speed centrifuges.

Following the suspended solid removal, the permeate stream is, in one embodiment, subjected to a carbon dioxide flash comprising a cylindrical vessel which separates a vapour phase containing mainly carbon dioxide, water vapour and a small amount of ammonia from the permeate stream. In another embodiment the permeate stream is fed directly to an ammonia removal unit. In yet another embodiment, the permeate stream is recycled back to the pre-treatment system or to the digester.

The temperature of the permeate stream prior to the carbon dioxide flash is raised to a high temperature just below the boiling point of the liquid, for example at least about 70° C., more preferably to a range between 80° C. and 95° C., by passing the liquid through two heat exchangers. In one embodiment, the first heat exchanger is regenerative and the second is powered by the biogas produced from the biogas digester. The carbon dioxide flash reduces the $CO_2$ content in the liquid up to 75% and raises the pH, thereby reducing the amount of sodium hydroxide, potassium hydroxide or any other suitable base addition needed in a subsequent step. Further, the carbon dioxide flash reduces the size of the subsequent ammonia stripper required.

In one embodiment, the carbon dioxide flash process is performed at an elevated pressure on the feed side. At the entrance of the flash unit a pressure reducing valve affects the pressure drop in the unit splitting the permeate stream into a gas and a liquid phase. The pressure is provided by the pump transporting the liquid to the flash unit.

Following the carbon dioxide flash, the flash effluent is pumped into an ammonia removal unit.

In one embodiment, prior to the ammonia removal process, sodium hydroxide is added to the flash effluent/filtrate permeate/mechanical separation liquid effluent to increase the pH of liquid.

Although the permeate from the filtration can, in principle, be treated directly in a reverse osmosis unit, in practice this leads to significant difficulties in the reverse osmosis due to a rather high concentration of ammonia (between 2500 and 4000 ppm) in the ammonia rich effluent. According to the present invention, it has been found that effective removal of ammonia, together with carbon dioxide, is critical for the success and economical operation of the subsequent reverse osmosis step. Various methods and apparatuses for the removal of ammonia are known in the art, and the precise nature of the ammonia stripper used is not critical.

However, the inventors herein have found that a significantly improved result is obtained when the ammonia stripping step is performed at an elevated temperature, and optionally also under a partial vacuum. While not wishing to be bound by any theory, the improved results obtained when the ammonia stripping is performed with the application of heat are believed to be related to the following equilibrium equations for ammonia and carbon dioxide:

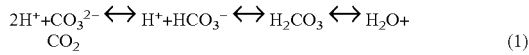

$$2H^+ + CO_3^{2-} \leftrightarrow H^+ + HCO_3^- \leftrightarrow H_2CO_3 \leftrightarrow H_2O + CO_2 \quad (1)$$

$$NH_4^+ \leftrightarrow NH_3 + H^+ \quad (2)$$

With increased temperature, the equilibrium for carbonic acid/carbon dioxide is shifted to the right, i.e. towards release of gaseous carbon dioxide. This is accompanied by a decrease in the $H^+$ concentration, i.e. an increase in pH, which in turn shifts the ammonium/ammonia equilibrium to the right, i.e. towards conversion of dissolved ammonium to ammonia. Similarly, the conversion of ammonium to ammonia shifts the carbonic acid/carbon dioxide equilibrium towards conversion to carbon dioxide. Thus, the application of heat serves to improve the removal of both ammonia and carbon dioxide, and the effect can be further improved if the process is carried out under a partial vacuum.

Addition of base increases the pH and shifts the carbonic acid/carbon dioxide to the left, i.e. towards formation of bicarbonate and carbonate. The ammonium/ammonia equilibrium, at the addition of base and as an increase in pH, shifts to the right, i.e. towards conversion of dissolved ammonia, as when the temperature is increased. Addition of base serves to improve the removal of only ammonia and not carbon dioxide.

Accordingly, in the present invention, ammonia stripping is typically performed at a temperature of at least about 60° C., preferably at least about 70° C., more preferably at least about 85° C., e.g. at least about 90° C. The liquid may also be boiled so that ammonia stripping is obtained by means of distillation. Optionally, a combination of heat and reduced pressure may be used, e.g. a pressure of about 0.25-0.75 bar, such as about 0.5 bar, and a temperature of about 65-85° C., such as about 70-80° C.

The removal of ammonia is important for several reasons. One of these is the fact that removal of ammonium in the subsequent reverse osmosis step is relatively poor compared to many other inorganic salts. Thus, it will typically not be possible to remove more than about 90-95% of the ammonium ions by means of reverse osmosis, while reverse osmosis can, for example, remove about 99.5% of sodium ions present. As a result, if ammonia is not sufficiently removed by ammonia stripping, the water obtained following reverse osmosis will contain an excessive amount of ammonia, i.e. an amount exceeding that allowed by relevant laws and standards. In addition, the removal of almost all of the ammonia (about 98-99%) provides the advantage of separating the ammonia from salts of phosphorus and potassium, which makes these end products more useful and valuable.

As will be understood by the skilled artisan upon reading this disclosure, the ammonia stripping method used is not critical, and various methods known in the art can be adapted for use in the methods and plants of the present invention.

A nonlimiting example of a suitable ammonia stripping method and apparatus is described in EP 0494154-A.

In one embodiment, heat and reduced pressure are both provided by a compression evaporator, the heat being provided by condensation of evaporated liquid.

As an alternative to the use of a combination of heat and reduced pressure, the removal of ammonia and any remaining carbon dioxide can also be obtained using heating alone at, for example, atmospheric pressure. In this embodiment, the feed liquid is simply heated to a temperature sufficient to distil off the ammonia and carbon dioxide. In this embodiment, the means for heat can be powered by the biogas produced from the biogas digester.

One embodiment of the present invention involves using a commercially available air stripper method comprised of a tower filled with a suitable packing material such as described at http://www with the extension .rvtpe.net/en/packing-honeycombs of the World Wide Web. The liquid feed stream is introduced in the top of the tower via a distributor providing for an even distribution of the liquid over the packing material, while a stream of ammonia free air is introduced in the bottom of the tower counter-currently to the feed liquid stream. Contact between the feed liquid and the air results in a transfer of ammonia and possibly carbon dioxide from the feed liquid to the air stream. When base has not been added to the liquid stream, carbon dioxide may be transferred to the air stream by the very low solubility of carbon dioxide at the elevated temperature in the stripper unit. This results in an increase of the pH of the solution due to the shift in the equilibrium. The elevation of the pH to a value of about 9-10 is sufficient to increase the amount of ammonia on the expense of ammonium ions to a level, where ammonia is transferred from liquid to gaseous phase. When base has been added to the liquid stream, carbon dioxide is bound in the liquid as bicarbonate/carbonate. The pH value of the liquid stream will be in the range of efficient ammonia stripping from the beginning and ammonia is transferred from liquid to gaseous phase. Carbon dioxide will in this case not be transferred to the air stream. The air is in both cases subsequently transferred to an absorber tower filled with a suitable packing material, where the air containing ammonia and possibly carbon dioxide is counter currently mixed with an acid, preferably, but no way limited to, sulphuric acid, at a pH of about 2 to 3.5. When the air to the absorber column does not contain carbon dioxide, the air leaving the absorber column is recycled directly back to the stripper column. When carbon dioxide has been transferred to the air stream in the stripper unit, carbon dioxide is prevented from absorption in the acid due to the low pH. The carbon dioxide leaves the absorber column with the air stream and a fraction of the air leaving the absorber is purged. Make-up air (corresponding to the purged amount of air) without ammonia and low carbon dioxide content is added prior to the stripping column. This will prevent the air going to the stripper from being saturated with carbon dioxide. The ammonium sulphate product resulting from the absorption process, which is at a concentration of about 38%-mass, is either sold directly or subsequently dried and crystallised and sold as a valuable nitrogen and/or sulphate fertilizer.

In one embodiment, after the ammonia stripping unit, the stripped effluent is led to a waste water treatment plant. Alternative examples of uses for the stripped effluent include, but are not limited to, land irrigation, process water in industries or further treatment in a reverse osmosis filtration unit.

The exhaust gas stripped from the mechanical separation liquid effluent/filtrate permeate in the carbon dioxide flash typically contains a smaller portion of ammonia. Accordingly, ammonia must be removed from this exhaust gas prior to release as exhaust of this amount of ammonia would not only constitute a loss of ammonia but also create an undesirable environmental impact. The present invention provides several options for usage of this gas. In one embodiment the carbon dioxide flash gas is sent to an odour treatment for a removal of ammonia. In this embodiment, the ammonia in the gas is lost. In another embodiment, the flash gas is sent to an acid-absorber resembling the absorber described in the ammonia stripping unit. After the odour or acid absorber treatment, the flash gas can be released to the ambient. In another embodiment, the flash gas (treated and/or untreated) is used as an acidifier in a subsequent step.

Since the removal of ammonia and possibly carbon dioxide from the mechanical separation liquid effluent/permeate filtrate is accompanied by an increase in pH, the liquid exiting the ammonia stripper, referred to herein as stripped effluent, typically has a pH value about 9-10. In the possible subsequent reverse osmosis step, a lower pH is desired in order to prevent deposits on the membrane. Accordingly, the pH of the stripped effluent is reduced to below about 7.0 prior to the reverse osmosis step. Typically, the pH is adjusted to about 6.5. Any suitable acid may be used. In one embodiment, an inorganic acid is used. Examples of acids to be used include, but are not limited to phosphoric acid, nitric acid, hydrochloric acid, phosphoric acid and sulphuric acid. A preferred acid is citric acid.

Alternatively, the biogas from the digester and/or the carbon dioxide flash gas is used as an acidifier. In one embodiment, the ammonia free liquid from the stripper is pumped to a scrubber tower filled with a suitable packing material such as described at issuu.com with the extension /rvtpe/docs/rvt_tower_packings/3?mode=embed&documentId=090121110652-5cecce3f946e479d9a012d0feabef a99&layout=grey of the world wide web. As will be understood by the skilled artisan upon reading this disclosure, alternative packing materials used for ammonia strippers and absorbers can also be used. The liquid is fed to the top of the tower and mixed with biogas and/or flash gas introduced in the bottom of the tower counter-currently with the ammonia free liquid. In another embodiment the biogas/flash gas is mixed into the liquid via passive mixing.

$CO_2$ in the biogas/flash gas acts as an acid in accordance with the following set of equations:

$$CO_2 + H_2O \leftrightarrow HCO_3^- + H^+$$

$$H^+ + OH^- \leftrightarrow H_2O$$

Pilot scale trails have shown that the biogas from a given process always contains carbon dioxide sufficient for a neutralization of the ammonia free liquid, which after ammonia stripping and preliminary carbon dioxide flash has a very low buffering capacity, from a pH around 10 to a pH around 6.5. An important advantage arises from this neutralising action when biogas is used for the neutralization process as a part of the carbon dioxide in the biogas is removed leaving the biogas with a higher methane ratio. This higher methane ratio is beneficial in subsequent utilization of the biogas as fuel for gas motors and power generation.

Subsequent to neutralization, the neutralized liquid can, but in no way limited to, be led to a waste water treatment plant, used for land irrigation, used as process water in industries or be treated further in a reverse osmosis filtration unit. The liquid following ammonia stripping, now depleted in salts, allows for a final reverse osmosis treatment to work with a very high efficiency, resulting in a much improved recovery and a cleaner reverse osmosis permeate of purer water than is obtainable by currently available processes. After having passed through the ammonia stripper, the ammonia free liquid consists of a nutrient salt fraction in which essentially all ammonia, phosphate and carbon dioxide have been removed, the pH of the nutrient salt fraction having been adjusted to a suitable level as described above. This nutrient salt fraction is then subjected to further purification using a membrane separation technique, in particular a reverse osmosis unit, which performs the final step in the treatment process, namely the separation of nutrient salts to result in a fertilizer concentrate fraction and a water fraction. The nutrient salts removed in this step are salts of potassium which serve as a fertilizer product. The water that remains after the reverse osmosis step is clean, potable water that meets the World Health Organization (WHO) requirements for drinking water.

In one embodiment of the present invention, the reverse osmosis step is performed using a conventional spiral reverse osmosis membrane unit arranged in a tapered configuration. In one embodiment, the membranes are of the polyamide brackish water type normally used for desalination.

The reverse osmosis may be performed as a continuous process or a batch process. In one embodiment, the reverse osmosis is performed as a fed batch process. This can, for example, take place using a concentrate tank with a volume of about 2 m³. At the beginning of a cycle, the concentrate tank is filled up with the neutralized liquid (feed water) which is pumped to the reverse osmosis membrane. Clean water is removed from the reverse osmosis unit, while salts retained by the reverse osmosis membrane are returned to the concentrate tank for further processing. After a period of, for example, about 12-14 hours, the volume of concentrate in the tank has been reduced to, e.g., about 20% of the original feed water volume. At this point, the fertilizer concentrate is removed from the tank, which is then rinsed prior to the start of a new cycle.

The present invention further provides a plant for conducting this waste treatment method. Embodiments of the plant are depicted in schematics in FIGS. 1 and 2. A mass balance diagram for one embodiment of the plant is depicted in FIG. 3.

Figure 2:
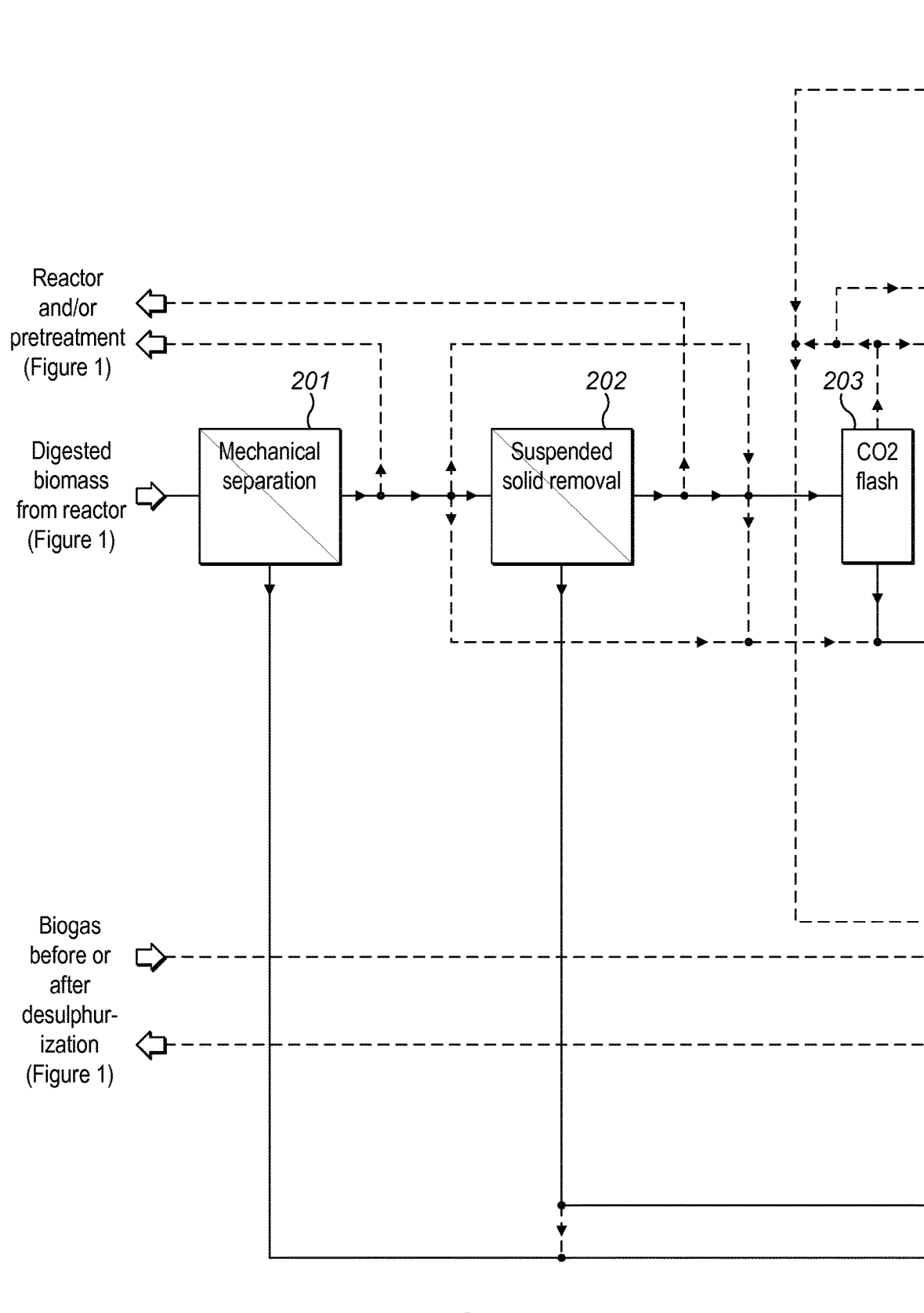
FIG. 2 shows components of one embodiment of the digestate separation process including mechanical separation, suspended solid removal, carbon dioxide flash, ammonia air-stripping, $H_2SO_4$-absorption, neutralization, reverse osmosis filtration and odour treatment. Different alternative embodiments of the process are shown in this figure.
Figure 2:
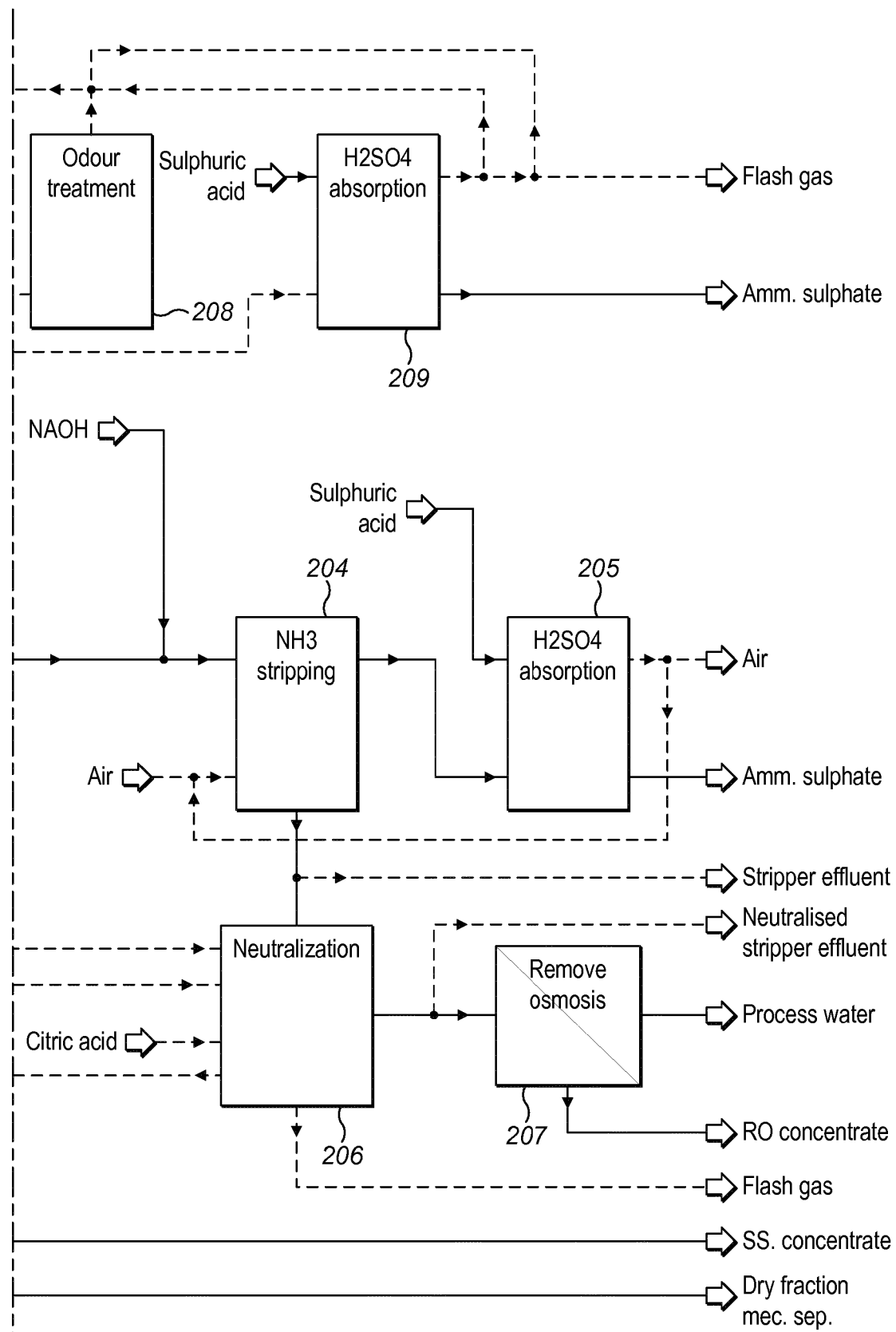
Figure 3:
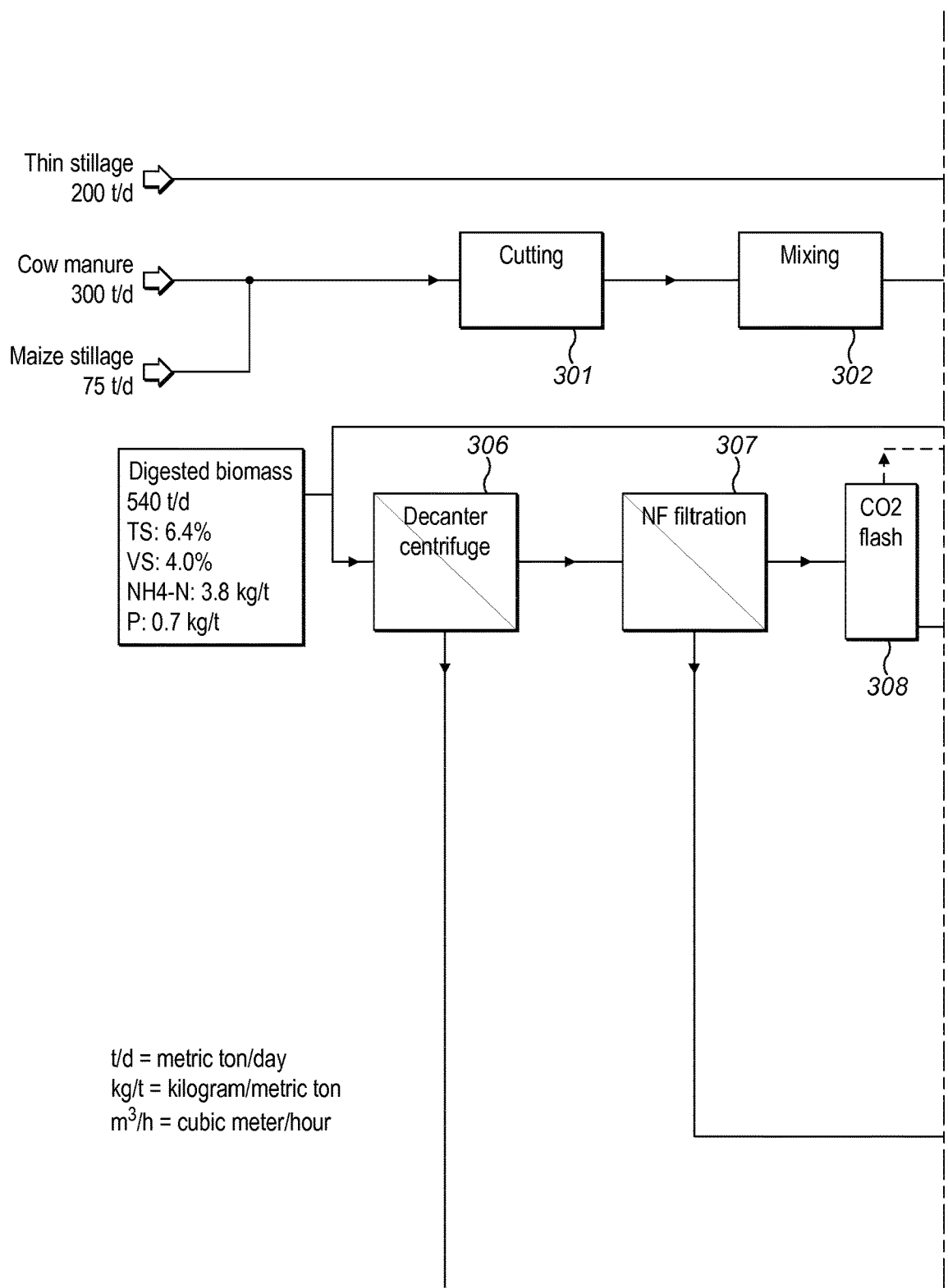
FIG. 3 shows a mass balance diagram of one embodiment of the present invention. In this embodiment cow manure, maize silage and thin stillage is fed to a digester. Cow manure and maize silage is macerated/shredded and mixed prior to the anaerobic digestion. Thin stillage is fed directly to the digester. The biogas produced in the digestion process is desulfurized and converted to heat and power in a combined heat and power unit (CHP). The digestate leaving the anaerobic digestion is led to the separation process containing a decanter centrifuge, nano-filtration, carbon dioxide flash, ammonia air-stripping, $H_2SO_4$-absorption, neutralization with citric acid and reverse osmosis filtration.
Figure 3:
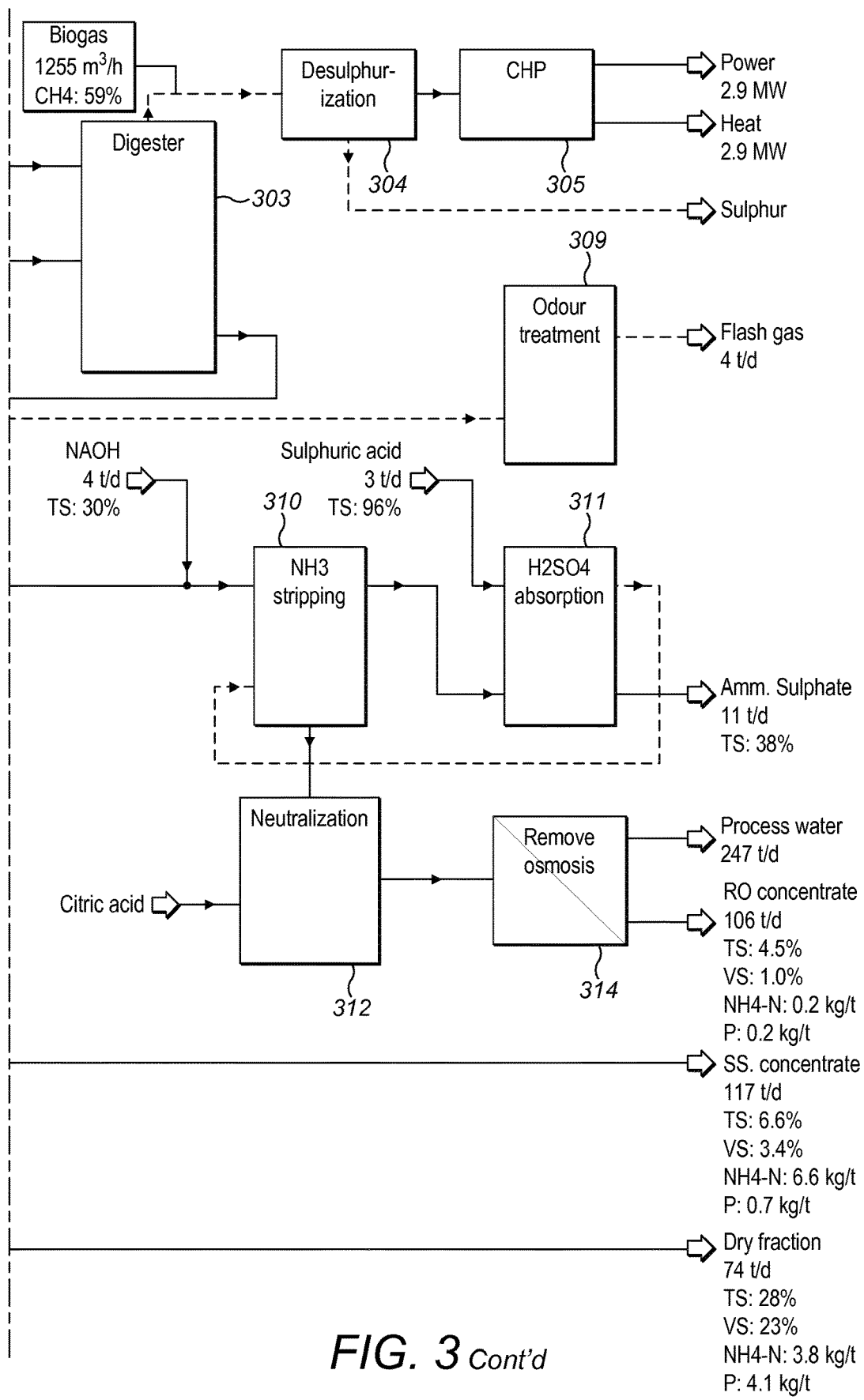

As will be understood by the skilled artisan upon reading this disclosure, alternative equipment as well as alternative configurations of the equipment in the plant to those depicted in FIGS. 1, 2 and 3 may be used and such alterations are considered as part of this invention.

FIG. 1, is a diagram showing the basic components of one embodiment of the biogas process of the present invention. Organic material possibly containing impurities (such as glass, batteries, plastic items, and metal) and/or effluent from the mechanical separation and/or permeate from the suspended solid removal is fed to the system where it can be led straight to the biogas digester 107 and/or through one or several of the pre-treatment processes including, but not limited to sorting 101 for impurity removal, cutting 102, thermal treatment 103, crushing 104 and/or extruding 105, in any order. Pre-treated material, untreated organic material, effluent from the mechanical separation and/or permeate from the suspended solid removal can also be led to a mixing tank 106 prior to entering the digester 107. From the mixing tank 106 the organic material can be led back to pre-treatment processes 101-105 or to the digester 107, wherein the anaerobic fermentation takes place. An outlet at or near the top of the digester 107 allows biogas to be removed from the digester. The biogas can be used later in the process as an agent for neutralizing the basic liquid originating from the ammonia stripping operation or treated in a desulphurization unit 108 for removal of hydrogen sulphide. The biogas leaving the desulphurization unit 108 can as well be used as an agent for neutralizing the basic liquid originating from the ammonia stripping operation. In another embodiment the biogas is led to a combined heat and power plant (CHP) 109, for energy and heat production. In another embodiment, the biogas is led to a boiler 110 for heat production only. In yet another embodiment the biogas is led to a biogas upgrading plant 111 for methane purification.

FIG. 2 shows the basic components of one embodiment of the digestate separation process wherein the digestate from the digester 107 (depicted in FIG. 1) is led to a mechanical separation process 201. The digestate is split into a dry fraction, which in cases where decanter centrifuges are used, contains up to 75% of the phosphorous plant and a thin fraction. The dry fraction can be used as fertilizer. The thin fraction is either led back to the digestion process (depicted in FIG. 1) and/or a pre-treatment process (depicted in FIG. 1), or sent to a $CO_2$ flash 203, an ammonia stripping column 204, or to a means for additional suspended solid removal process 202. Examples of means for additional suspended removal include, but are not limited to, membrane filtration with a microfiltration, membrane filtration with ultra filtration or membrane filtration with nano filtration.

In the suspended solid removal process 202, the liquid is again split into a concentrate fraction and a thin permeate fraction. The thin permeate fraction has no or low suspended solid content. The concentrate fraction is removed from the suspended solid separation process and in some cases blended with the dry fraction from the mechanical separation. The thin permeate fraction is either led back to the digestion process (depicted in FIG. 1) or a pre-treatment process (depicted in FIG. 1), or sent to an ammonia stripping column 204 or a $CO_2$ flash 203.

In the $CO_2$ flash 203, the liquid is split into a vapour fraction and a liquid fraction with a lower carbon dioxide content and therefore higher pH than the liquid fed to the $CO_2$ flash 203. The vapour contains a small portion of ammonia and is either led to a means for odour treatment 208, a first acid-absorber means 209 or a neutralization process 206 in a subsequent step. A nonlimiting example of a means for odour treatment is a biofilter. A nonlimiting example of a means for acid absorption such as $H_2SO_4$ absorption is an absorption column. The liquid fraction is led to an air ammonia stripping column 204.

Prior to the ammonia stripping column 204, sodium hydroxide can be added to the stripping feed to increase pH and bind the remaining carbon dioxide as bicarbonate/carbonate. In the ammonia stripping process, ammonia is removed from the liquid with an air stream fed counter-currently to the feed liquid stream. Air containing ammonia is removed at the top of the stripping column 204 and led to a second acid-absorber 205 where it is fed counter-currently with respect to the acid used. In the second acid-absorber 205, ammonia is transferred from the air to the liquid creating an ammonium acidate product of approximately 38%-mass. A nonlimiting example of an ammonium acidate product is ammonium-sulphate. However, as will be understood by the skilled artisan upon reading this disclosure, use of alternative acids including, but not limited to hydrochloric acid, phosphoric acid, nitric acid, citric acid or acetic acid will results in alternative ammonium acidate products. Ammonium sulphate which is removed from the bottom of the column has fertilizer value. The air leaving the top of the second acid-absorber 205 is free of ammonia and recycled back to the ammonia stripper column 204. In some embodiments, a fraction of the air leaving the absorber is purged. Prior to the ammonia stripper 204, additional air corresponding to the fraction purged is added to the air recycled to the ammonia stripper 204. The liquid leaving the ammonia stripper 204, referred to in FIG. 2 as stripper effluent, either leaves the plant or is led to a neutralization unit 206, where it is blended with an acid such as, but not limited to citric acid or acetic acid, biogas or flash gas directly from the flashing process or after the absorption or odour treatment. The neutralized liquid, referred to as neutralized stripper effluent in FIG. 2, either leaves the plant or is led to a reverse osmosis unit 207 where it is split into a fertilizer concentrate fraction comprising salts of potassium, referred to as RO concentrate in FIG. 2 and clean water of drinking water quality, referred to as process water in FIG. 2.

FIG. 3 is a nonlimiting example showing schematically the result of processing 300 ton/day of cow manure, 75 ton/day of maize silage and 200 ton/day of thin stillage in a plant of the present invention. Cow manure and maize silage is macerated/shredded 301 and mixed 302 prior to the anaerobic digestion 303. Thin stillage is fed directly to the digester 303. Processing of the organic waste in the biogas digester results in 1255 $Nm^3$/hour of biogas, of which about 59% is methane. After anaerobic digestion, the digestate is led to a decanter centrifuge 306 creating a compost fraction of 73.6 ton/day and a reject water fraction which is led to a nano-filtration unit 307. A concentrate fraction of 116.6 ton/day and a permeate fraction free from suspended solids are created in the nano-filtration unit 307. The permeate is led to a $CO_2$ flash 308, where $CO_2$ is removed in a flash gas. Flash gas is led to an odour treatment unit 309 and then to the ambient. Flash effluent is led to an ammonia stripper column 310, where ammonia is recovered in a $H_2SO_4$- absorber column 311 as 11 ton/day ammonium sulphate. NaOH is added prior to ammonia stripping to secure that the pH is in a range for optimal stripping. In this nonlimiting example, stripped effluent was neutralized with citric acid 312 and led to a reverse osmosis filtration unit 314. Process water, 247.4 ton/day, and RO concentrate, 106.0 ton/day, is produced in the RO unit 314. In FIG. 3, VS=volatile solids, TS=total solids.

The separation of the manure or other organic waste into the various end products (clean water, ammonium sulphate, K fertilizer concentrate, P fertilizer fibrous compost and biogas) according to the method and plant of the present invention results in a significant improvement in the utilization of the various components in the waste material, and correspondingly a significant reduction of the environmental impact. In this way, it is in fact possible to recycle as much as 98-100% of the organic matter in liquid manure into useful products. Furthermore, the invention makes it possible to obtain significant improvements in the internal environment of stalls containing livestock, since the stalls can be designed for immediate removal of liquid manure. As a result, it is possible to essentially eliminate ammonia from such stalls, and such stalls can be constructed without any large-scale storage facilities for liquid manure, since the manure can be led out of the stall for substantially immediate treatment.

A further important advantage of the method and treatment plant of the present invention is that it is designed to require very little maintenance. This is in particular due to the effective removal of ammonia and carbon dioxide, thereby preventing damage to the reverse osmosis membrane.

Since very little routine maintenance is required, the entire system is well-suited for automatic, computerized operation. For example, the fermentation process can be monitored by means of automatic measurements of volatile fatty acids, such measurements typically being performed downstream of the separator, e.g. using an automatic titration process. The results of these measurements can then be used to automatically regulate the feed of untreated waste into the biogas digester, so as to maintain a desired organic matter content in the biogas digester and thus an optimum fermentation rate.

What is claimed is:

1. A method for the treatment of an organic waste material inclusive of fibres, said method comprising:
   (a) subjecting waste inclusive of fibres to anaerobic fermentation in a biogas digester;
   (b) mechanically separating effluent from the biogas digester into a concentrated fraction and a liquid fraction;
   (c) heating the liquid fraction to a high temperature below the boiling point of the liquid;
   (d) introducing the heated liquid to a flash column to partially remove volatile carbon dioxide and to elevate pH of the liquid;
   (e) pumping flash liquid heated to a temperature of at least 60° C. from step (d) into an ammonia removal unit and removing ammonia from the liquid under reduced pressure of 0.25-0.75 bar following carbon dioxide removal so that 98-99% of ammonia is removed;
   (f) neutralizing the ammonia free liquid of step (e) with biogas, flash gas or acetic or citric acid; and
   (g) treating the neutralized ammonia free liquid in a reverse osmosis unit to obtain a potassium rich fraction useful as a fertilizer concentrate and a clean water fraction.

2. The method of claim 1, further comprising adding sodium hydroxide to the heated and flashed liquid of step (d) prior to removal of ammonia in step (e).

3. The method of claim 1, wherein the waste is pre-treated prior to anaerobic fermentation by sorting for impurity removal, cutting, thermal treatment, crushing and/or extruding.

4. The method of claim 1, wherein in step (c) the liquid effluent stream is heated to a temperature of at least about 70° C. before removing the carbon dioxide in step (d).

5. The method of claim 1, further comprising subjecting the liquid fraction obtained by mechanical separation in step (b) to a further suspended solid removal process.

6. The method of claim 1, further comprising
   (i) recycling the liquid fraction from step (b) to the biogas digester and repeating step (a); and/or
   (ii) recycling the liquid fraction from step (b) through pre-treatment and further anaerobic fermentation.

7. The method of claim 5, further comprising recycling any liquid fraction following the further suspended solid removal process through pre-treatment and further anaerobic fermentation.

8. The method of claim 1, further comprising subjecting the carbon dioxide from the flash column in step (d) to odour treatment and/or $H_2SO_4$ absorption.

* * * * *